United States Patent [19]
Boutos

[11] Patent Number: 5,782,902
[45] Date of Patent: Jul. 21, 1998

[54] APPARATUS FOR STIMULATING LIVING TISSUE

[76] Inventor: David Boutos, 4420 Dunlap Crossing St., Las Vegas, Nev. 89129

[21] Appl. No.: 782,786

[22] Filed: Jan. 13, 1997

Related U.S. Application Data

[63] Continuation-in-part of Ser. No. 568,875, Dec. 7, 1995, Pat. No. 5,697,966, and Ser. No. 369,172, Jan. 5, 1995, Pat. No. 5,571,118.

[51] Int. Cl.$^6$ ........................................................ A61N 1/05
[52] U.S. Cl. ................................................ 607/143; 607/138
[58] Field of Search .................................. 607/118, 115, 607/143, 149, 138; 600/382, 384, 386

[56] References Cited

U.S. PATENT DOCUMENTS 5,571,118 11/1996 Boutos .................................. 607/138
5,697,966 12/1997 Boutos .................................. 607/138

*Primary Examiner*—Scott M. Getzow
*Attorney, Agent, or Firm*—Meschkow & Gresham, P.L.C.; Jordan M. Meschkow; Lowell W. Gresham

[57] ABSTRACT

Electrodes for stimulating living tissue such as penile, scrotal, anal, vaginal and clitoral tissue are shown. The electrodes are formed from elastomeric material. Electrical stimulation to such areas is intended to control incontinence, to induce penile erection, or to induce excitation and orgasm. Three embodiments of a tube electrode formed from elastomeric material, have a nonconductive base, and a conductive tube weaving through holes in the base. Two have single adjustable loops and are for use around penile or scrotal tissue, and against anal tissue. The third comprises two loops, one to wrap each testicle against scrotal tissue.

17 Claims, 4 Drawing Sheets

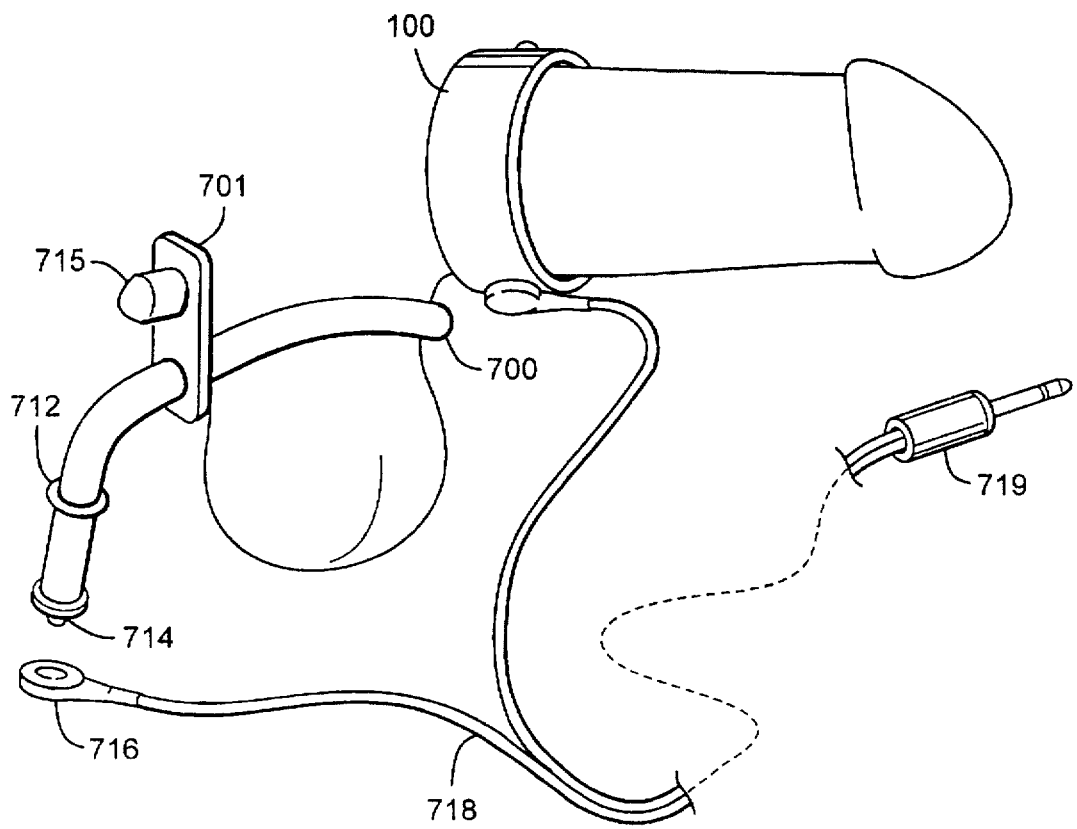
FIG. 6
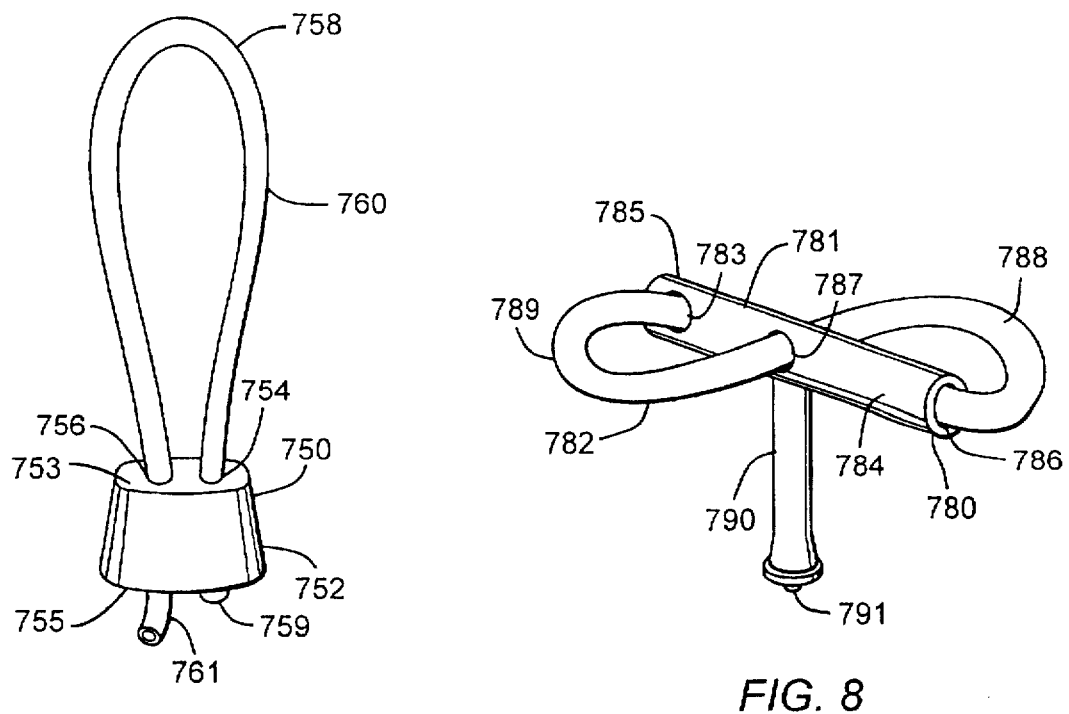
FIG. 7
FIG. 8

APPARATUS FOR STIMULATING LIVING TISSUE

RELATED APPLICATION

This application is a Continuation-In-Part of "Apparatus for Stimulating Living Tissue" invented by David Boutos, Ser. No. 08/568,875, filed Dec. 7, 1995, now U.S. Pat. No. 5,697,966 and "Apparatus for Stimulating Penile, Scrotal, Anal, Vaginal and Clitoral Tissue" invented by David Boutos, Ser. No. 08/369,172, filed Jan. 5, 1995, issued Nov. 5, 1996 as U.S. Pat. No. 5,571,118.

BACKGROUND OF THE INVENTION

1. Field of the Invention

This invention relates to apparatus for applying electrical energy to living tissue.

More particularly, the present invention relates to apparatus for electrically stimulating penile, scrotal, anal vaginal and clitoral tissue.

In a further and more specific aspects, the invention relates to electrically stimulating penile, scrotal, vaginal and clitoral tissue for the purposes of treating incontinence in men and women, and for inducing penile erection, male and female orgasm.

2. Prior Art

It is widely known that the application of electrical stimulation to certain neuromuscular areas in or near the genitalia can be used to treat incontinence in both men and women. Also known is that the application of electrical stimulation to penile tissue can cause erection where impotence may exist due to physiological or psychological conditions. Additionally it is known the application of electrical stimulation to penile, vaginal, clitoral, anal, or prostate tissue can induce orgasm, even where the subject has suffered vascular degenerative neural neuropathy. Finally it is known that diabetes and many other medical disorders can cause penile impotence.

The art is replete with various apparatus used to apply electrical stimulation to the subject areas. Rigid rings capable of transmitting low levels of electricity to the skin and muscles are typically applied about the penis and/or the scrotum. Insertable rolled or plug-type electrodes, made to be rolled to size, or sized in a variety of sizes to fit the user's anatomy, are known for the purpose of applying low levels of electricity to the skin and muscles inside and surrounding the vagina and the anus.

Urinary incontinence is a common problem that may require long term retraining of self-control, particularly after a stroke, or permanent use of an external control device. The prior art does not teach of apparatus that is designed to be worn while the user, fully dressed, moves about his or her everyday course of events.

Rigid rings are useable for males where the application of electrical current to only a portion of penile tissue is sufficient to induce urethral control or erection. This is because sufficient expansion room is required within the ring to accommodate penile engorgement. Rigid rings are particularly problematic where penile atrophy has occurred, and the desired goal is erection or orgasm. The tremendously varying size of the penile tissue from rest to engorgement may cause a need to use a large diameter ring on a small diameter penis, or to change rings during a treatment.

For the female, a discrete unit, usable in a variety of ways, is desirable to control incontinence, or to stimulate and to induce orgasm. Such a unit should be particularly designed to be worn under a user's clothing, and operative while the female was engaged in other normal everyday activity.

It would be highly advantageous, therefore, to remedy the foregoing and other deficiencies inherent in the prior art.

Accordingly, it is an object of the present invention to provide improvements in electrical stimulation apparatus for both men and women.

Another object of the invention is the provision of improvements especially adapted for use in connection with apparatus for controlling and treating incontinence in men and women.

And another object of the invention is to provide improved means for the application of electrical stimulation to the vagina.

Yet another object of the invention is to provide means for the application of electrical stimulation to the penile and scrotal tissue.

Yet still another object of the invention is the provision of improved means for the application of electrical stimulation to the penile and scrotal tissue that can expand with penile erection.

A further object of the instant invention is to provide improvements in the connectivity of electrical stimulation apparatus.

And a further object of the invention is the provision of a male and female electrical stimulation apparatus that can be worn comfortably and discretely under a user's clothing.

Yet a further object of this invention is to provide male electrical stimulation apparatus that can induce erection and orgasm, and female electrical stimulation apparatus that can induce orgasm.

And yet an object of the invention is the provision of means and improvements according to the foregoing which will materially reduce the cost of male and female electrical stimulation apparatus.

SUMMARY OF THE INVENTION

Briefly, to achieve the desired objects of the instant invention in accordance with a preferred embodiment thereof, provided is a first tube electrode to which a source of electricity may be attached. The tube electrode is mounted in a holding plate with two holes. A first end of the tube, electrode is fixed to the holding plate in one hole, and held in position at the second hole of the holding plate by an O-ring, allowing the tube electrode to be sized about an object.

The tube electrode is fabricated from elastomeric material. It may be wrapped about penile or scrotal tissue, or inserted into the vagina and positioned therein to control incontinence, or so the application of electricity may induce excitation and orgasm.

A second tube electrode like the first may be inserted anally instead thereby stimulating that tissue and the nearby prostate for assisting in controlling incontinence, or for excitation. This second tube electrode uses a wedge instead of a holding plate, thereby preventing the device from traveling too far into the anal cavity.

A third electrode in the form of a tube is for direct use on scrotal tissue and comprises another alternate embodiment of the invention. The tube is also formed from elastomeric material, and has a second tube it mounts through to form a figure-8 shape suitable to wrap around the testicles.

BRIEF DESCRIPTION OF THE DRAWINGS

The foregoing and further and more specific objects and advantages of the instant invention will become readily apparent to those skilled in the art from the following detailed description of a preferred embodiment thereof taken in conjunction with the drawings, in which:

FIG. 6 shows the tube electrode in use in combination with another electrode;

FIG. 7 is a view of a alternate tube electrode designed for anal use;

FIG. 8 is a perspective view of a third tube electrode designed for wrapping around each testicle;

PREFERRED EMBODIMENT OF THE PRESENT INVENTION

Figure 1:
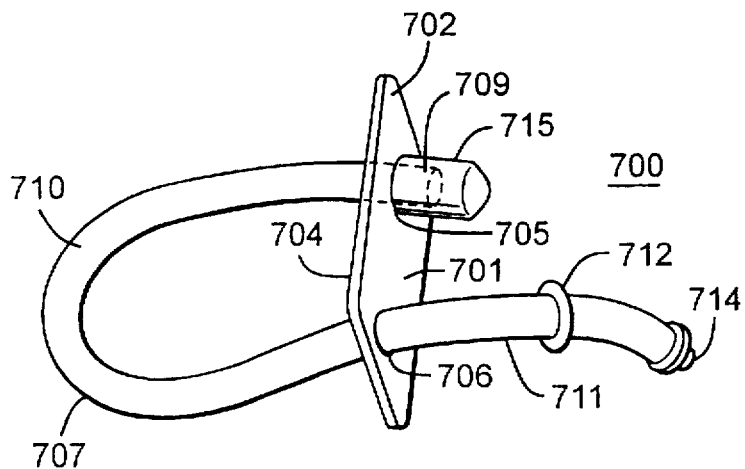
FIG. 1 is a side view of a tube electrode in accordance with the present invention.
Figure 2:
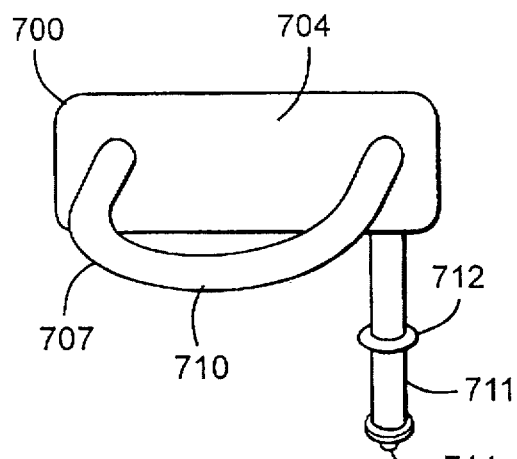
FIG. 2 is a perspective view of the tube electrode shown in FIG. 1.

Turning now to the drawings in which like reference characters indicate corresponding elements throughout the several views, attention is first directed to FIGS. 1 and 2 where tube electrode 700 is shown. Tube electrode 700 is fabricated from elastomeric material such as silicon, viton, and neoprene, and such material is substantially non-conductive of electricity.

Tube electrode 700 has base plate 701, which has first side 702 and second side 704. Extending therethrough base plate 701 is first hole 705 and second hole 706.

Tube 707 is disposed through said base by inserting each of its two ends in first and second holes 705 and 706. When tube 707 is so disposed, it comprises a first tube section 709 extending through first hole 705 from the first side of base plate 701, a second tube section 710 extending from second side 704 at hole 705 to second hole 706 and forming a loop (also referred to herein as loop 710), and a third tube section 711 extending through second hole 706 from the first side of base plate 701.

Tube 707 is conductive of electricity. It is made conductive by embedding carbon particles in the silicon, viton, or neoprene during fabrication of tube 707.

FIG. 2 shows tube electrode 700 specifically showing second side 704. In this view, third tube section 711 is bent downwardly so it shows in FIG. 2.

By virtue of the configuration of tube 707 and base plate 701, the length of loop 710 and third tube section 711 are inversely adjustable. That is the longer one makes third tube section 711 by pulling tube 707 through base plate 701 in the direction of second side 704 to first side 702, the shorter one makes loop 710. Vice versa, the longer one makes loop 710 by pulling tube 707 through base plate 701 in the direction of first side 702 to second side 704, the shorter one makes third tube section 711.

In one embodiment of tube electrode 700 (shown), first tube section 709 is fixed to base plate 701 with silicon adhesive or other method, thereby allowing loop 710 to be lengthened or shortened against base plate 701 only by pulling or pushing third tube section 711 against base plate 701. In this embodiment, first tube section 709 may be covered with a substantially non-conductive cover 715 which allows tube electrode 700 to be manipulated even when electrified.

In another embodiment (not shown) first tube section 709 has length and is not fixed to base plate 701 allowing loop 710 to be lengthened or shortened against base plate 701 by either pulling or pushing first tube section 709 against base plate 701, or pulling or pushing third tube section 711 against base plate 701, or by pulling or pushing both first and tube sections 709 and 711 against base plate 701.

As shown, third tube section 711 carries O-ring 712. O-ring 712 may be slid along the length of third tube section 711 against base plate 701 thereby preventing loop 710 from increasing in length. In the not-shown embodiment, first tube section 709 may also carry an O-ring to prevent loop 710 from increasing in length by virtue of the shortening of first tube section 709.

Tube 707 also has contact 714 attached at one end. As shown, contact 714 is embedded into tube 707 at third section 711. Tube 707 will conduct electricity when it is connected to a source of electricity, typically a controller allowing for adjustment of current (not shown). The controller will typically include a jack, and a wire connected to the jack. The wire will typically terminate with a female snap connector. Such female snap connector is connected to snap connector 716, shown in FIG. 6.

Figure 3:
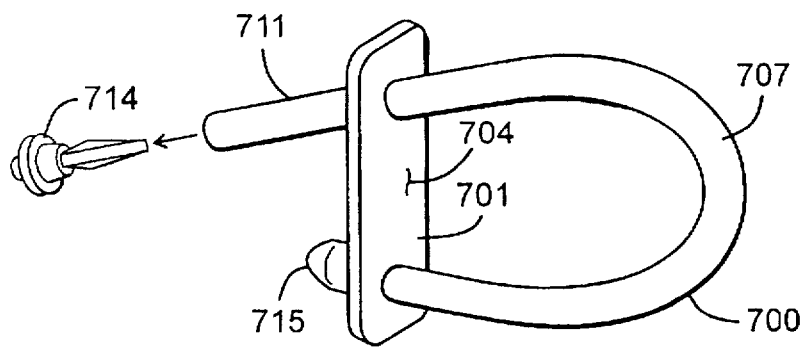
FIG. 3 shows the contact of the tube electrode being removed.
Figure 4:
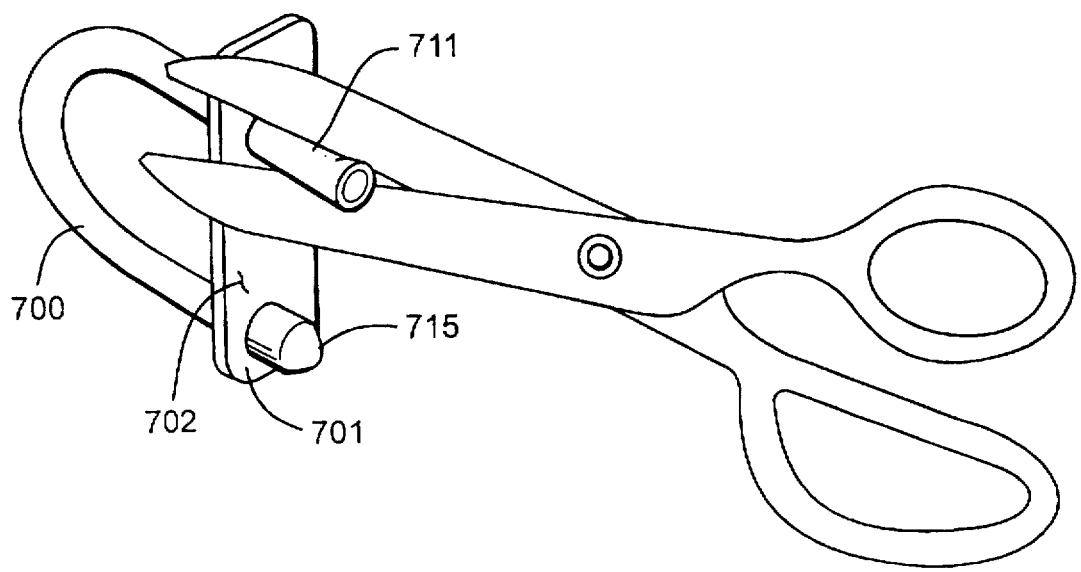
FIG. 4 shows the tube electrode being cut to size.
Figure 5:
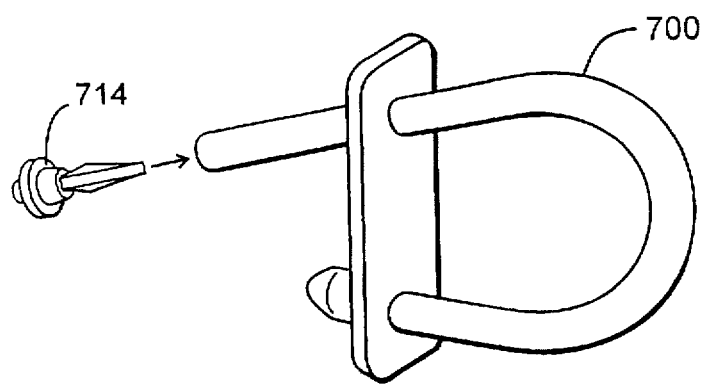
FIG. 5 shows the contact of the tube electrode being replaced.

Tube electrode 700 may be kept in its original adjustable-to-many-sizes form, or it may be cut to size for a user. Turning to FIGS. 3–5, a method for cutting tube electrode 700 is shown. First, contact 714 is removed from third section 711. Then third section 711 is cut using a scissors or other cutting device (as shown), and contact 714 is replaced.

FIG. 6 shows tube electrode 700 applied to the scrotal tissue, while ring electrode 100 is applied to penile tissue. Tube electrode 700 could be applied to penile tissue as well, and is particularly effective at causing erection or orgasm when in position on the penis, such as when loop around the base of the penis, or at the back of the head of the penis.

Running directly to and connected to snap connector 716 is conductive line 718. Line 718 has plug connector 719 which connects electrodes 100 and 700 to an electrical supply box (not shown here, but shown in parent case application Ser. No. 08/369,172).

Shown in FIG. 7 is tube electrode 750. Tube electrode 750 has wedge 752 as its base, and carries tube 758 therein. The usual use of tube electrode 750 is for stimulation of the anal tissue. Tube 758 is inserted anally while wedge 752 prevents tube electrode 750 from creeping further into the anal cavity.

Wedge 752 has first side 753 and second side 755, and holes 754 and 756 running from first side 753 to second side 755. Holes 754 and 756 of wedge 752 carry tube 758. As tube 707 has three sections, tube 758 has first section 759, which extends through hole 754 (and may either be carried in entirety within hole 754 or extend beyond wedge 752 and second side 755), second section or loop 760 extending between holes 754 and 756 on first side 753, and third section 761 which extends through hole 756 beyond wedge 752 and second side 755.

Pulling third section 761 in the direction of first side 753 to second side 755 causes third section 761 to grow in length, with a corresponding shortening in length of loop 760, while pushing third section 761 into wedge 752 causes a corresponding increase in length of loop 760. Loop 760 and third section 759 therefore have an inverse "change in length" relationship. Loop 760 should be adjustable to be longer than is comfortable while in the anal cavity with wedge 752 against the cheeks of the buttocks.

Either first section 759 or third section 761 will carry an electrical contact like electrical contact 714. First section 759 may be fixed to wedge 752 by adhesive so that loop 760 may be adjusted by manipulating third section 761 further out of or in to wedge 752.

Figure 9:
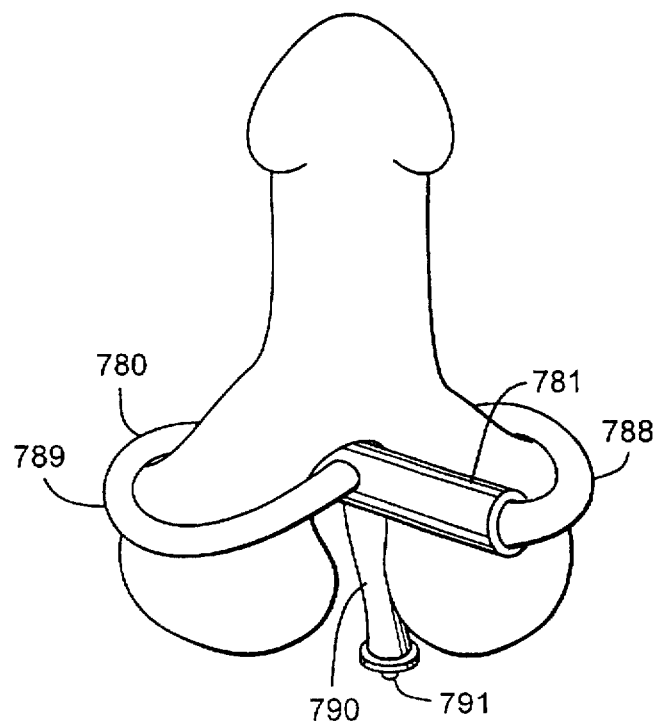
FIG. 9 shows the third tube electrode wrapping around each testicle.

Tube electrode 780 is shown in FIG. 8. Although very similar to the other embodiments shown, tube electrode 780 has two loops, first loop 788 and second loop 789 each of which can be wrapped around and tightened down on scrotal tissue around each of the testicles (as shown in FIG. 9).

Electrode 780 has base 781 carries tube 782. Base 781 has first side 784 and second side 785, and holes 783 and 787 running through base 781 from first side 784 to second side 785.

Base 781 also has hole 786 in one end. In this embodiment as shown, tube 782 has a first section 788 which has an end buried within hole 786. In an alternate embodiment (not shown) hole 786 would be through base 781, and first section 788 could travel through base 781 from second side 785 to first side 784.

Like with tube electrode 700, tube electrode 780 has third section 790 extending through 783 on second side 785, and loop 789 (like loop 710) formed on first side 784. Also like tube electrodes 700 and 750, third section 790 is contiguous with second section or loop 789 thereby having an inverse "change in length" relationship, relative to base 781. Electrical contact 791 may be connected to an electrical supply device via a line with connectors like that shown in FIG. 6.

Yet in this embodiment, loop 789 is first loop 789 because first section 788 also forms second loop 788. Since second loop 788 is contiguous with first loop 789, second loop 788 may be adjusted to size (thereby shortening or lengthening first loop 789), and then third section 790 may be adjusted to adjust the size (or length) of first loop 789. This way as shown in FIG. 9, tube electrode 780 may be wrapped around the testicles.

FIG. 9 shows base 781 positioned against scrotal tissue between the testicles, while first loop 789 is wrapped around and tightened down against the testicle on the left, and second loop 788 is wrapped around and tightened down against the testicle on the right. Contact 791 remains ready for connection to an electrical supply (not shown).

Figure 10:
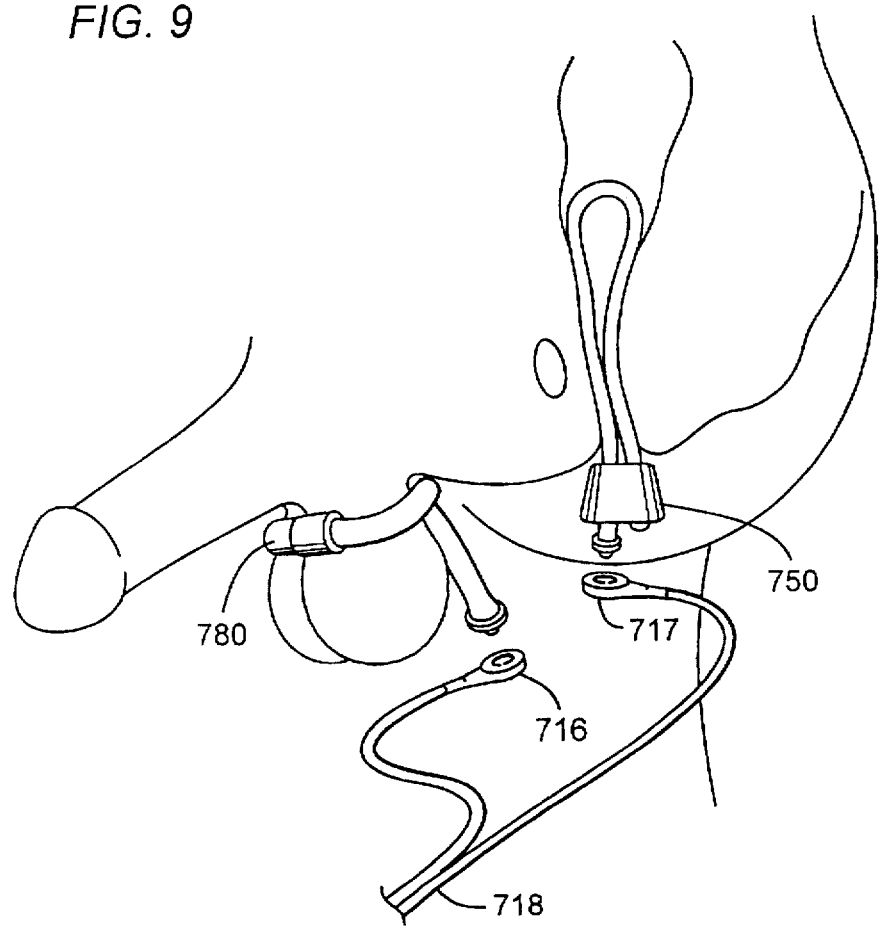
FIG. 10 shows the alternate tube electrode of FIG. 7 in use in combination with the third tube electrode of FIG. 8.

Tubular electrode 780 is shown in use with tubular electrode 750 in FIG. 10. In this view, electrode 780 is wrapped around each of the testicles in the manner before proscribed, while tube electrode 750 is placed anally. When connected to an electrical supply this mode of use provides extremely effective control of incontinence because the application of current to both these areas provides significant contraction of the muscles required to control male urination.

Various changes and modifications to the embodiments herein chosen for purposes of illustration will readily occur to those skilled in the art. To the extent that such modifications and variations do not depart from the spirit of the invention, they are intended to be included within the scope thereof which is assessed only by a fair interpretation of the following claims.

Having fully described the invention in such clear and concise terms as to enable those skilled in the art to understand and practice the same, the invention claimed is:

1. An electrode apparatus comprising:
    a base having at least first and second sides and first and second holes running from said first side to said second side;
    a tube electrode disposed through said base wherein:
        a first section of said tube electrode extends from the first side of said base plate from said first hole;
        a second section of said tube electrode extends from the second side of said base plate from said first hole and to said second hole forming a loop; and
        a third section of said tube electrode extends from the first side of said base plate from said second hole.
2. The electrode apparatus of claim 1 wherein said tube electrode is conductive of electrical current.
3. The electrode apparatus of claim 1 wherein said base is substantially non-conductive of electrical current.
4. The electrode apparatus of claim 1 wherein first section of said tube electrode is fixed to said base, and the length of said loop and said third section of said tube electrode are inversely adjustable relative said base.
5. The electrode apparatus of claim 4 wherein said third section of said tube electrode carries an O-ring;
    wherein said O-ring can be adjusted against said base thereby preventing the lengthening of said loop.
6. The electrode apparatus of claim 4 further comprising a substantially non-conductive cover over said first section of said tube electrode.
7. The electrode apparatus of claim 1 wherein the length of said first and said third section of said tube electrode are inversely adjustable in length relative said base, and the length of said loop and said first and third sections of said tube electrode is inversely adjustable relative said base.
8. The electrode apparatus of claim 7 wherein said first and third sections of said tube electrode each carry an O-ring;
    wherein said O-rings can be adjusted against said base thereby preventing the lengthening of said loop.
9. The electrode apparatus of claim 1 wherein said base is a plate.
10. The electrode apparatus of claim 1 wherein said base is a block of material forming a wedge.
11. The electrode apparatus of claim 1 further comprising an electrical contact that plugs directly into one end of said tube.
12. The electrode of claim 1 wherein said loop is a first loop and said base further comprises a third hole and said first section of said tube electrode connects with said base into said third hole;
    wherein said first section of said tube electrode forms a second loop on the first side of said base.
13. The electrode of claim 12 wherein said third hole is in an end of said base and said first section of said tube electrode connects with said base within said third hole.
14. The electrode of claim 12 wherein the length of said first loop and said third section of said tube electrode are inversely adjustable relative said base.
15. The electrode apparatus of claim 14 wherein said third section of said tube electrode carries an O-ring;
    wherein said O-ring can be adjusted against said base thereby preventing the lengthening of said first loop.
16. The electrode apparatus of claim 15 wherein the length of said first loop and said second loop are inversely adjustable relative said base.
17. An electrode apparatus comprising:
    a base having at least first and second sides and first and second holes running from said first side to said second side;
    a tube electrode disposed through said base wherein:
        a first section of said tube electrode is disposed within said base plate in said first hole;
        a second section of said tube electrode extends from the second side of said base plate from said first hole and to said second hole forming a loop; and
        a third section of said tube electrode extends from the first side of said base plate from said second hole.

* * * * *